United States Patent [19]

Pullukat et al.

[11] 4,383,119
[45] May 10, 1983

[54] ORGANOMAGNESIUM COMPOUNDS

[75] Inventors: Thomas J. Pullukat, Hoffman Estates; Raymond E. Hoff, Palatine, both of Ill.

[73] Assignee: Chemplex Company, Rolling Meadows, Ill.

[21] Appl. No.: 384,885

[22] Filed: Jun. 4, 1982

[51] Int. Cl.³ ............................................. C07F 7/10
[52] U.S. Cl. .................................. 556/412; 556/410
[58] Field of Search ............................ 556/410, 412

[56] References Cited
FOREIGN PATENT DOCUMENTS
1158973 12/1963 Fed. Rep. of Germany ...... 556/412

Primary Examiner—Paul F. Shaver
Attorney, Agent, or Firm—Wood, Dalton, Phillips, Mason & Rowe

[57] ABSTRACT

The new compounds represented by the formulas:

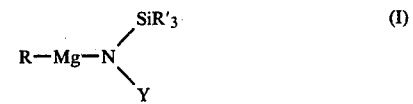

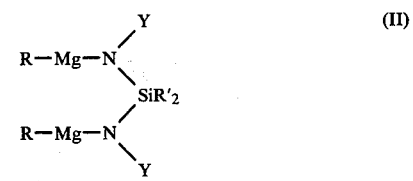

in which R is a straight or branched chain alkyl group including alkyl groups of about 1–18 carbon atoms, aryl groups of about 6 to 14 carbon atoms, and the R's are the same or different. The alkyl or aryl R groups are preferably unsubstituted but may have inert substituents that are nonreactive to the highly reactive Mg-N bonds, preferred substituents being ether groups, tertiary amine groups, chloride and fluoride groups and combinations of these, R' is R or hydrogen, Y is R or —SiR'$_3$, all R's are the same or different, all R' are the same or different and all Y are the same or different.

8 Claims, No Drawings

ORGANOMAGNESIUM COMPOUNDS

BACKGROUND OF THE INVENTION

It is well known that organomagnesium compounds, as exemplified by Grignard reagents, have great utility in organic synthesis. For example, Grignard reagents can convert ketones into tertiary alcohols. However, in many cases, only a portion of the ketone is converted into the desired tertiary alcohol, the remainder appearing as a mixture of secondary alcohol and an enol. The extent of these side reactions depends upon the polarity (electron density) of the R-Mg bond.

Consequently, it is a feature of this invention to provide an organomagnesium reagent that, among its advantages, diminishes secondary alcohol and enol formation in the synthesis of tertiary alcohols from ketones.

This feature has great utility in biochemical reactions where it is often important to conserve materials and control the stereochemistry of the addition.

In this connection, another feature of this invention is to provide a series of organomagnesium compounds in which the molecular size can be readily changed merely by changing the silylamide group.

These compounds may be used as catalysts, for example, in polymerizing and copolymerizing 1-olefins.

SUMMARY OF THE INVENTION

The new organomagnesium compounds of this invention are stable, usually soluble in hydrocarbon solvents, and are convenient to use. The compounds of the series are new compositions of matter having the structural formulas:

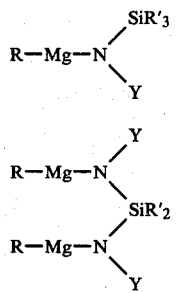

in which R is a straight or branched chain alkyl group including alkyl groups of about 1-18 carbon atoms, aryl groups of about 6 to 14 carbon atoms, and the R's are the same or different. The alkyl or aryl R groups are preferably unsubstituted but may have inert substituents that are nonreactive to the highly reactive Mg-N bonds, preferred substituents being ether groups, tertiary amine groups, chloride and fluoride groups and combinations of these, R' is R or hydrogen, Y is R or -SiR'$_3$, all R's are the same or different, all R' are the same or different and all Y are the same or different.

Desired species are:

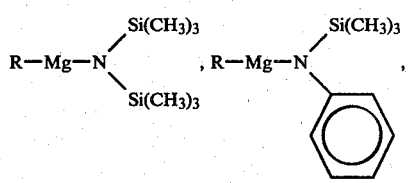

wherein R is straight or branched chain alkyl of about 2–8 carbon atoms;

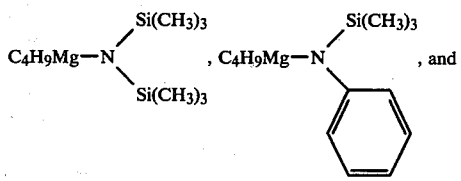

between each of the two C$_4$H$_9$-N so that the structural formula will read as follows:

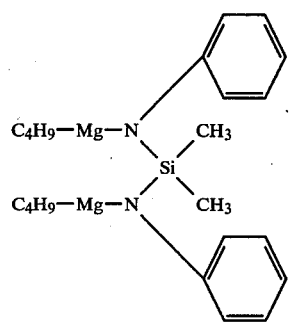

These compounds may be complexed with other organometallic compounds such as alkyl aluminum, alkyl boron and alkyl zinc. This complexing changes the characteristics of the compounds of this invention such as their solubility in hydrocarbons.

Dialkylmagnesium compounds have been reacted with conjugated 1,3 diolefins to form polymers of narrow molecular weight distribution. Because the alkyl magnesium silylamides of this invention can exist as molecular species in hydrocarbon solvents, they can be used as initiators of anionic polymerization of 1,3-butadiene and isoprene to form polymers with distinctive distributions of 1,2- and 1,4-addition, and cis and trans unsaturation.

Another use of the organomagnesium compounds of this invention is as catalysts in the polymerization of styrene and methyl methacrylate as well as the oligomerization and polymerization of 1-olefins such as ethylene at elevated pressures.

The organomagnesium compounds of this invention have great utility in the formation of olefin polymerization catalysts by reaction of the organomagnesium compound with transition metal compounds, especially those of titanium, vanadium, chromium, and zirconium.

The previous organomagnesium compounds most readily available and wellknown are the reagents discovered by Victor Grignard in 1900. These reagents are the general disadvantages that they require an ether solvent and the presence of a halogen. The ether tends to decrease the reactivity of the alkyl-magnesium bond by coordination, and in anionic polymerization, the ether alters the cis to trans ratio of poly (1,3-dienes).

When attempts are made to prepare ether-free Grignard reagents, by removing the ether solvent or by the reaction of alkyl halides with magnesium in the absence of ether, the result is a viscous mixture of dialkylmagnesium and magnesium dihalides. When the alkyl groups are methyl, ethyl, propyl and butyl, the dialkylmagnesium compounds are difficult to separate from the also-insoluble magnesium dihalides because of their insolubility in hydrocarbons. The dialkylmagnesium compounds are thermally unstable and cannot be separated by thermal distillation.

The alkyl magnesium silylamides of this invention are in many cases soluble in hydrocarbons and can be obtained without any halogen content.

This invention provides organomagnesium compounds which not only have reactive alkyl magnesium bonds but are also stable. These new compounds do not require an ether solvent as Grignard reagents do. Ethers are undesirable in many cases because the coordination of the ether diminishes the reactivity of the alkyl magnesium bond and in some cases, changes the nature of the product. An example of this latter effect is the alteration of the steric structure of polybutadiene.

The organomagnesium compounds of this invention are superior to the dialkylmagnesiums of methyl, ethyl, n-propyl, and n-butyl in that they dissolve more easily in hydrocarbon solvents to give less viscous solutions.

The new compounds of (I), above, have only one reactive alkyl magnesium bond unlike the recently discovered solutions of butyl ethyl magnesium, sec-butyl-n-butyl magnesium and similar mixtures.

No complexing agent is required for the organomagnesium compounds of this invention to induce hydrocarbon solubility.

The reactivity of any particular alkyl group bonded to the magnesium can be modified by the structure of the silylamino portion of the compound. This cannot be done with previously known organomagnesium reagents.

DESCRIPTION OF THE PREFERRED EMBODIMENTS

The organomagnesium compounds of this invention can be made by any of many possible methods. One very convenient method of synthesis is to combine a silylamine which has an acidic N-H group with a mixed dialkyl magnesium compound solution, such as a solution of butyl ethyl magnesium. The silylamine N-H will displace the most reactive alkyl group as in:

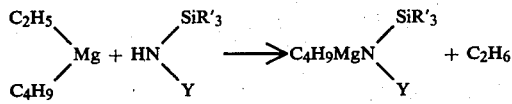

The following synthesis methods can also be used:
(1) A trialkylsilyl chloride is combined with a primary amine in the presence of a tertiary amine to trap HCl. To the reaction mixture a solution of dialkylmagnesium is added. Precipitated tertiary amine hydrochloride is filtered out to give a chloride and ether-free solution of alkyl magnesium silylamide. This method synthesizes a silylamine by known methods without requiring that the silylamine be separated from the reaction mixture.
(2) The following procedure using the reaction of a Grignard reagent with a lithium silylamide may also be used:

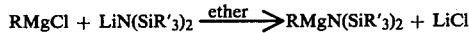

After the addition of the lithium silylamide to the Grignard reagent in ether, a hydrocarbon solvent with a higher boiling point than the ether is added. The ether is then removed as by distillation. The lithium chloride is then removed as by filtration.
(3) When the ether is removed from a Grignard reagent, a solid residue remains. Extraction of this residue with a solution of silylamine provides an ether and halide free solution of alkyl magnesium silylamide.
(4) Magnesium metal, an alkyl halide, and a silylamine can be coreacted in an aromatic or aliphatic hydrocarbon to yield an alkyl silylamide.

EXAMPLE 1

Synthesis of Butyl Magnesium Bis(trimethyl silyl)amide

A 25 ml volume of butyl ethyl magnesium solution in heptane containing 16 mmoles of magnesium compound was transferred by syringe through a septum into a dry, capped, nitrogen-filled crown top bottle. In the same manner, 3.3 ml of hexamethyl disilazane (16 mmoles) were added, and the mixture was stirred one hour at room temperature. After this hour a quantity of the solution was applied to the surface of a salt plate inside a glove bag inflated with nitrogen. The solvent was evaporated from the surface of the salt plate with a stream of nitrogen. Another salt plate was sealed over the face of the first salt plate and an infrared spectrum of the deposited layer was obtained. This reaction product had almost no absorption at 3380 cm$^{-1}$ which is due to the N-H bond of hexamethyl disilazane. In addition, the product had an absorption at 992 cm$^{-3}$ not present in the spectrum of either reactant.

A sample of the gas in the bottle was analyzed by gas chromatography. Butane and ethane were found but comparison with the gas above the stock solution of the butyl ethyl magnesium solution indicated an enrichment in ethane due to the reaction.

Consequently, this example shows that the N-H bond of hexamethyl disilazane is consumed in a reaction with a solution of butyl ethyl magnesium to form a new product.

EXAMPLE 2

Synthesis of Butyl Magnesium Bis(trimethyl silyl)amide

A Fischer-Porter test tube size aerosol compatability vessel was fitted with a tee and valves to maintain a nitrogen atmosphere. A 25 ml volume of the same butyl ethyl magnesium solution used in Example 1, and 3.3 ml hexamethyl disilazane were injected by syringe into the tube. Gas evolved when there was contact between the two reactants. After one hour and 40 minutes at room temperature, the contents of the tube were transferred without exposure to air to a flask for solvent evaporation. After about four hours at room temperature under N$_2$ flow, crystals began to appear in the viscous residue. The next morning, the residue appeared to be completely solidified. Vacuum was applied for two hours. When the pressure was first lowered, the material in the flask frothed.

At the end of the two hours under vacuum the flask was immersed in a water bath which was slowly heated. The solid melted between 50° and 60° C. to a very viscous liquid. The clear liquid at 80° C. was vacuum treated for an additional period then cooled to room temperature. After five minutes at room temperature, the product became cloudy and viscous. A sample of the wax-like product was sent to a commercial analysis laboratory. The element content of the sample, and the calculated element content of butyl magnesium bis(- trimethyl silyl)amide are given below in weight percent:

|  | Sample | Calculated |
|---|---|---|
| carbon | 49.51 | 49.7 |
| hydrogen | 11.35 | 11.2 |
| nitrogen | 5.53 | 5.8 |
| magnesium | 9.89 | 10.1 |
| silicon | 23.17 | 23.2 |

The excellent agreement between the element contents found for the sample and calculated for butyl magnesium bis(trimethyl silyl)amide supports the conclusion that

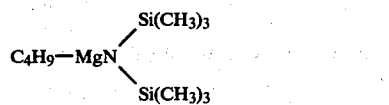

was prepared.

EXAMPLE 3

Synthesis of Butyl Magnesium Trimethylsilylphenylamide

In a Fischer-Porter tube as described in Example 2, 25 ml of a butyl ethyl magnesium solution in heptane was mixed with 2.8 ml of trimethylsilylaniline (16 mmoles, from Petrarch Systems, Inc.). There was rapid evolution of gas. Because butane would not be expected to bubble out of the liquid heptane phase at room temperature, the gas appeared to be ethane. After four hours and 41 minutes at room temperature, the content of the tube was transferred to a flask for solvent evaporation. The major part of the solvent was evaporated at 50° C. under a $N_2$ flow. The residue was vacuum treated for 15 minutes at 50° C. until the bubbling ceased. In a dry ice/acetone bath, the reaction product solidified to a clear glass, but did not crystallize.

The product was dissolved in hexane and a portion of the hexane solution was applied to a salt plate for an infrared spectrum as described in Example 1. The product dissolved rapidly and easily in hexane proving that the content of an exchange product such as di-n-butyl magnesium was very low.

The infrared spectrum showed that the product had no absorption at 3380 cm$^{-1}$ which is associated with the N-H bond of the trimethyl silylaniline.

The product when exposed to air rapidly becomes dark brown due to oxidation.

EXAMPLE 4

Synthesis of the Bis(butyl magnesium silylamide) of Bis(phenylamino) Dimethyl Silane A reaction was conducted between 16 mmoles of butyl ethyl magnesium solution in heptane and 8 mmoles of bis(phenylamino)dimethyl silane from Petrarch Systems, Inc. by the procedure described in Example 3. A yellow white precipitate formed and gas evolved when the two reagents were mixed. The white precipitate was applied to a salt plate as in Example 1, except that in this case after the evaporation of the solvent, the upper salt plate was rubbed against the lower one to make a thin uniform layer. Again the infrared spectrum showed no absorption due to N-H bond of the silylamine.

Because of the gas evolution, the formation of the precipitate, and the absence of N-H bonds in the precipitate, the precipitate appears to be a silylamide of the invention having the formula:

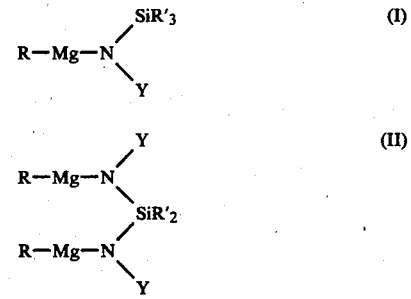

We claim:

1. The new compounds represented by the formulas:

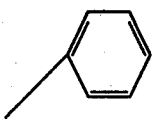

(I)

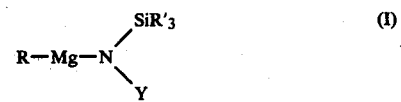

(II)

in which R is a straight or branched chain alkyl group of about 1–18 carbon atoms, aryl groups of about 6 to 14 carbon atoms, and the R groups are the same or different and may be unsubstituted but may, R' is R or hydrogen, Y groups is R or —SiR'$_3$, all R's are the same or different, all R groups are the same or different and all Y are the same or different.

2. The new compounds of claim 1 wherein said compounds comprise

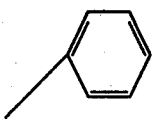

(I)

3. The new compounds of claim 1 wherein said compounds comprise

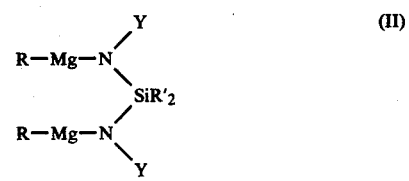

(II)

4. The new compounds of claim 1 having the formula:

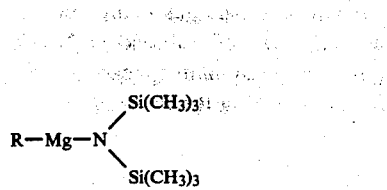
wherein R is straight or branched chain alkyl of about 2–8 carbon atoms.
5. The new compounds of claim 1 having the formula:
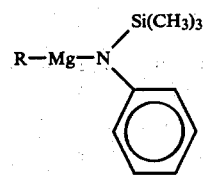
wherein R is straight or branched chain alkyl of 2–8 carbon atoms.
6. The new compounds of claim 1 having the formula:
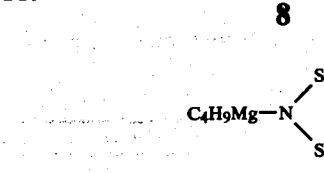
7. The new compounds of claim 1 having the formula:
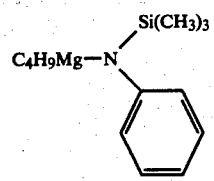
8. The new compounds of claim 1 having the formula:
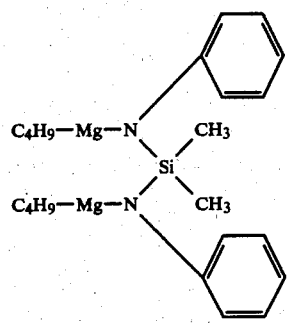
* * * * *

UNITED STATES PATENT AND TRADEMARK OFFICE
CERTIFICATE OF CORRECTION

PATENT NO. : 4,383,119

DATED : May 10, 1983

INVENTOR(S) : Thomas J. Pullukat and Raymond E. Hoff

It is certified that error appears in the above-identified patent and that said Letters Patent is hereby corrected as shown below:

Claim 1, line 42 after "may be" insert -- substituted or --;

Claim 1, line 42 after "unsubstituted" delete -- but may --;

Claim 1, line 43 delete "groups";

Claim 1, line 43 delete "R's" and insert -- R's -- in lieu thereof; and,

Claim 1, line 45 after "Y" insert -- groups --.

Column 2, lines 12 through 13, delete "between each of the two $C_4H_9$-N so that the structural formula will read as follows:".

Signed and Sealed this

Twenty-seventh Day of March 1984

[SEAL]

Attest:

GERALD J. MOSSINGHOFF

Attesting Officer     Commissioner of Patents and Trademarks